Feb. 19, 1974 M. B. WAKEFIELD Plant Pat. 3,482
DOGWOOD TREE
Filed June 29, 1972
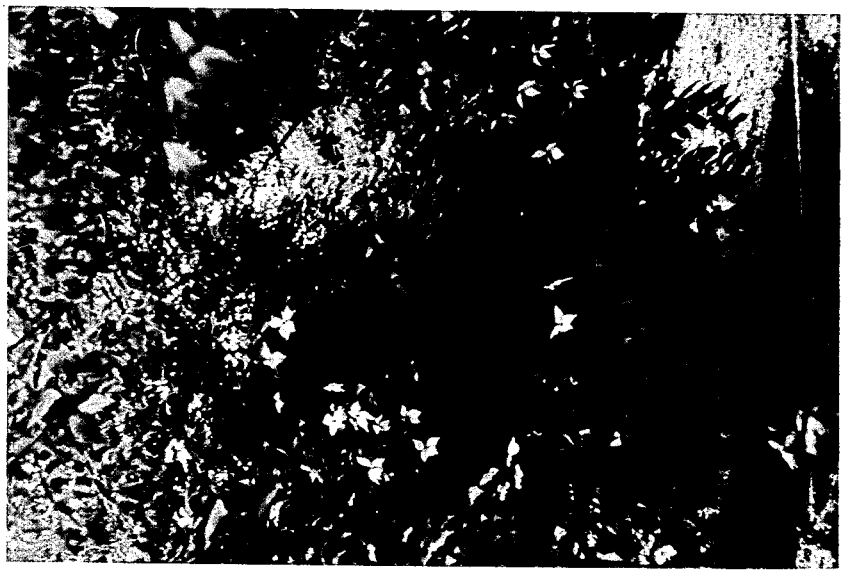
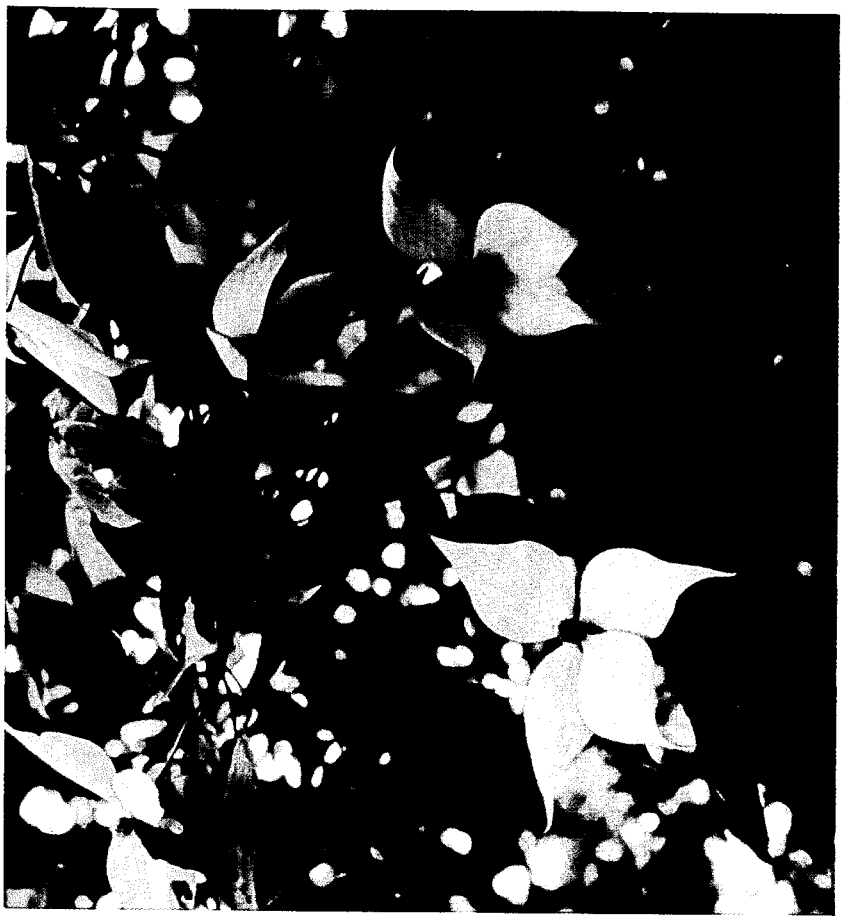

United States Patent Office

Plant Pat. 3,482
Patented Feb. 19, 1974

3,482

DOGWOOD TREE

Mary B. Wakefield, 1465 Brush Hill Road, Milton, Mass. 02186

Filed June 29, 1972, Ser. No. 267,515
Int. Cl. A01h *5/12*
U.S. Cl. Plt.—51 1 Claim

The present invention relates to a new and distinct variety of dogwood tree of the Japanese dogwood type botanically known as *Cornus kousa,* which was originated by me from seed which I initially processed and planted indoors, and subsequently set out as a young seedling in my outdoor experimental nursery maintained by me on my home property located at Milton, Mass.

At the time I acquired the original seed from which I developed this new dogwood variety, I was attending classes on plant propagation as conducted at the Arnold Arboretum which is near my home in Milton, Mass. My interest in plant propagation and experimentation led me to seek and receive permission to obtain seeds of various plants, including dogwoods, being grown at the Arnold Arboretum. This particular dogwood seed was one of many which were collected by me from a dogwood tree specimen of the kousa type, but of uncertain parentage, which had attracted my attention at the Arboretum aforementioned because of the exceptionally large size of the fruit borne thereby. In a few years after setting out and observing the new seedling in my nursery, I was particularly impressed by its strong, graceful and rapid habit of growth, and especially by the exceptionally large size of the flowers borne thereby and which consistently ranged from about 7 inches to 8 inches in diameter.

Continued observations of the original seedling and progeny thereof derived from rooted cuttings which I developed therefrom and planted in my nursery aforementioned, have convinced me, as well as the experts at the Arnold Arboretum, that my new seedling is a new and improved dogwood variety which is definitely distinguished from its parent variety and from all other varieties known to us, as evidenced by the following unique combination of features which are outstanding therein:

(1) A strong, graceful and rapid habit of growth;
(2) An exceptionally large bloom size ranging from about 7 inches to 8 inches in diameter;
(3) A distinctive bloom form characterized by a long, taper-pointing of the bracts which are carried on long peduncles so as to extend well beyond the foliage, with the peduncles being inclined from 30° to 60° above the branches so that the blooms are more readily visible to an observer standing nearby;
(4) A distinctive and interesting bloom color which begins as pale green and then whitens along the edges of the bracts, leaving a broad central green stripe longitudinally extending through each bract, and which remains for several weeks until the green color whitens and the bract color becomes white over-all;
(5) A prolonged blooming habit which usually begins in early June and extends well into July at Milton, Massachusetts, with the blooms remaining crisp and fresh until the bracts fall;
(6) Attractive fruit of large size which are borne on long, outwardly inclined peduncles and are readily visible from ground level;
(7) Excellent hardiness to at least —20° F. without injury; and
(8) Especial suitability for street plantings, as well as for ornamental plantings in parks and on residential grounds.

The accompanying drawing shows a typical tree specimen of my new dogwood variety, as well as typical foliage and bloom specimens on a larger scale.

The following is a detailed description of my new dogwood variety, with color terminology in accordance with the Royal Horticultural Colour Chart, published by the Royal Horticultural Society of London, except where general color terms of ordinary dictionary significance are obvious:

Parentage: Seedling of an unnamed and unpatented variety of the species *C. kousa* of uncertain origin and parentage.

Propagation: Holds its distinguishing characteristics through succeeding propagations by rooted cuttings.

Locality where grown and observed: Milton, Mass.

Tree: Strong, graceful and rapid habit of growth; grows to approximately 15 feet tall in about 10 years without fertilizing and is as tall as trees of other varieties growing nearby and which are 5 years older; hardy (has withstood temperatures as low as —20° F. without injury).

*Trunk.*—Slender; smooth.

*Branches.*—Slender; smooth. lower branches—Widespread and droop gracefully. Middle branches—Extend generally horizontally from trunk, then droop slightly and finally turn upwardly at tips. Upper branches.—Extend outward and upward at an angle of about 60°. Color—Near Grey Brown, No. 199A to 201B, with current year growth near Grey Brown, No. 199A to 199B all around.

*Leaves.*—Quantity—Abundant. Size—Length—from 4 inches to 5 inches; width—from 1¾ inches to 2 inches. Shape—From ovate to elliptic. Color—Green, near 144A, with third and fourth pairs of veins only having Dark Brown hairs, color near 200, in the axils; leaves turn deep red in color usually in November at Milton, Massachusetts. Margin—Obscurely crenate; somewhat undulate on edges near tip of leaf.

*Vegetative buds.*—Color—Near No. 200A.

Flower buds:

*Hardiness.*—Excellent; have withstood temperatures as low as —20° F. without injury.

*Size.*—Length—From about ¼ inch to 5/16 inch. Width—about 3/16 inch. Shape—Ovoid, with long, tapering acuminate tips. Color—Base color near No. 183A, covered with a whitish pubescence.

Flowers (inflorescence): Long-lasting and remain crisp and fresh until blooms drop.

*Dates of first and full bloom.*—About June 1 and June 15, respectively, with blooms continuing well into July at Milton, Mass., and being among the last of all dogwood blooms of this type to drop.

*Quantity.*—Normal for species.

*Size.*—Exceptionally large; most are about 7 inches in diameter, with some ranging as large as 8 inches in diameter.

*Petalage (bracts).*—4. Shape—Long, tapering and pointed. Size—Large. Length—from about 3¼ inches to 4 inches; width—from about 1¾ inches to 1⅞ inches. Color—Pale green at first and then gradually whiten at outer edges, leaving a broad central longitudinal green stripe which lasts for several weeks and then becomes white over-all.

Fruit:

*Borne.*—On long peduncles ranging from 3¾ inches to 4¾ inches long which extend at an outward and downward angle from the twigs so that the fruit is readily visible from ground level.

*Size.*—About 1 inch in diameter.

*Color.*—Begins green and then changes through yellow to bright red.

General observations

As the blooms age, the side bracts tend to point more downwardly at each side of the base, while their central areas widen and become forwardly protruding, with the upper bract remaining upright. This form is rather unique and interesting in a dogwood bloom. Throughout the blooming season, the peduncles on which the blooms are borne hold the blooms away from the branches, and as a consequence thereof and the unique bloom form, the upper flowers tend to face downwardly and their faces are directly presented to view from ground level even as the tree grows taller. This is contrary to the habit of other dogwood varieties which usually bear their flowers on the upper side of their branches and the flowers face upwardly so that only the bottoms of the flowers can be seen through the leaves when observed from ground level. These features, combined with the graceful form of the tree and the exceptionally large size and long-lasting qualities of the blooms, make my new dogwood variety especially suitable for street, park and home lawn plantings.

I claim:

1. A new and distinct variety of dogwood tree of the Japanese dogwood type, substantially as herein shown and described, characterized particularly as to novelty by the unique combination of a strong, graceful and rapid habit of growth, an exceptionally large bloom size ranging from about 7 inches to 8 inches in diameter, a distinctive bloom form characterized by a long, taper-pointing of the bracts which are carried on long peduncles so as to extend well beyond the foliage, with the peduncles being inclined from 30° to 60° above the branches so that the blooms are more readily visible to an observer standing nearby, a distinctive and interesting bloom color which begins as pale green and then whitens along the edges of the bracts, leaving a broad central green stripe longitudinally extending through each bract and which remains for several weeks until the green color whitens and the bract color becomes white over-all, a prolonged blooming habit which usually begins in early June and extends well into July at Milton, Massachusetts, with the blooms remaining crisp and fresh until the bracts fall, attractive fruit of large size which are borne on long, outwardly inclined peduncles and are readily visible from ground level, excellent hardiness to at least —20° F. without injury, and especial suitability for street plantings, as well as for ornamental plantings in parks and on residential grounds.

No references cited.

ROBERT E. BAGWILL, Primary Examiner